(12) United States Patent
Vermehren et al.

(10) Patent No.: US 7,026,477 B1
(45) Date of Patent: Apr. 11, 2006

(54) PROCESS FOR PREPARING SUBSTITUTED PHENYLSULFONYLUREAS FROM SULFONYL HALIDES

(75) Inventors: Jan Vermehren, Idstein (DE); Ernst Schmidt, Kastl (DE); Mark James Ford, Bad Soden (DE); Richard W. G. Foster, Hauxton (DE); Ian A. Bourne, Hauxton (DE)

(73) Assignee: Aventis CropScience GmbH, Frankfurt (DE)

( * ) Notice: Subject to any disclaimer, the term of this patent is extended or adjusted under 35 U.S.C. 154(b) by 179 days.

(21) Appl. No.: 10/089,288

(22) PCT Filed: Sep. 28, 2000

(86) PCT No.: PCT/EP00/09466

§ 371 (c)(1),
(2), (4) Date: Mar. 13, 2003

(87) PCT Pub. No.: WO01/23368

PCT Pub. Date: Apr. 5, 2001

(30) Foreign Application Priority Data

Sep. 28, 1999 (DE) .............................. 199 46 341

(51) Int. Cl.
*C07D 251/18* (2006.01)

(52) U.S. Cl. .................... 544/208; 544/215; 544/314; 544/316; 544/319; 564/84; 564/85; 564/86; 564/88

(58) Field of Classification Search ............... 544/208, 544/216, 314, 316, 319; 564/84, 85, 86, 564/88
See application file for complete search history.

(56) References Cited

U.S. PATENT DOCUMENTS

| | | | |
|---|---|---|---|
| 2,852,557 | A | 9/1958 | Schraufstatter |
| 4,238,621 | A | 12/1980 | Levitt |
| 4,849,010 | A | 7/1989 | Hillemann |
| 5,463,081 | A | 10/1995 | Ort et al. |
| 5,688,745 | A | 11/1997 | Ort et al. |

FOREIGN PATENT DOCUMENTS

| EP | 0 046 626 AW | 3/1982 |
|---|---|---|
| WO | 96/06826 | 3/1996 |

*Primary Examiner*—Venkataraman Balasubramanian
(74) *Attorney, Agent, or Firm*—Frommer Lawrence & Haug LLP

(57) ABSTRACT

The invention relates to a preparation process for a compound (I) or a salt thereof,

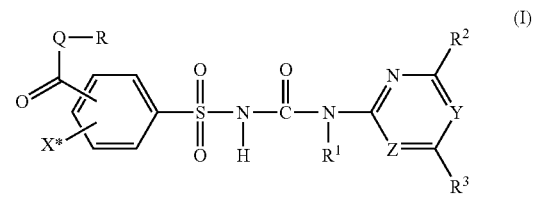

in which Q, X*, Y, Z, R, $R^1$, $R^2$ and $R^3$ are as defined in claim 1,

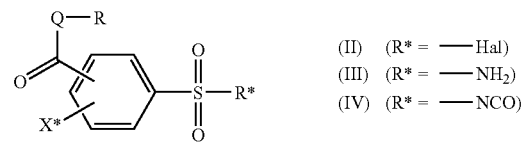

(II) (R* = —Hal)
(III) (R* = —$NH_2$)
(IV) (R* = —NCO)

which comprises
a) ammonolyzing a comp. (II) in which Hal=halogen atom to give (III), pref.
(a1) carrying out the reaction in an organic solvent mixture (org. solv. mixture) comprising (1) opt. halogenated aromatic hydrocarbons and (2) polar aprotic solvents, in a weight ratio of solv. (1): solv. (2) of 20:1 to 1:1,
(b) phosgenating the comp. (III) with phenylsulfonyl isocyanate of the formula (IV), pref.
(b1) in the case X*=halogen, carrying out the reaction with phosgene in an org. solv. in the presence of isocyanates R'-NCO as catalyst, where R'=(subst.) hydrocarbon, with or without addition of an amine base,
(c) reacting the resulting compound (IV) in org. solv. with the aminoheterocycle $H_2$N-Het (Het=heterocycle as in (I)) to give the comp. (I) or a salt thereof, pref.
(c1) carrying out the reaction in a solv. mixture of opt. halogenated arom. hydrocarbon having a b.p. of more than 110° C. and a polar aprotic solv., where at least one of the preferred partial steps (a1) to (c1) is carried out in the process.

20 Claims, No Drawings

PROCESS FOR PREPARING SUBSTITUTED PHENYLSULFONYLUREAS FROM SULFONYL HALIDES

The invention relates to the technical field of the chemical processes for preparing compounds from the group of herbicidal phenylsulfonylureas and intermediates thereof.

A number of substituted phenylsulfonylureas have been described as herbicides and plant growth regulators. Within the group of the phenylsulfonylureas, the synthesis of those having a carboxyl group or a group of a carboxylic acid derivative on the phenyl ring is particularly challenging. Of interest are the compounds known from EP-A-007687 or WO-A-92/13845 of the formula (I) and salts thereof,

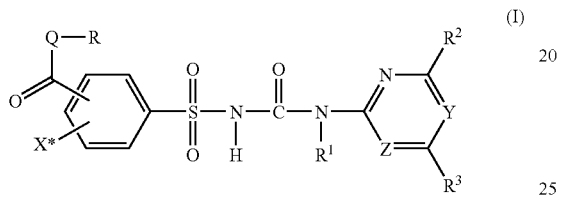

(I)

in which in which

Q is oxygen, sulfur or —N($R^4$)—,

X* is hydrogen, halogen, cyano, nitro, ($C_1$–$C_3$)-alkyl or methoxy, preferably hydrogen or iodine, in particular iodine, Y,Z independently of one another are CH or N, where Y and Z are not simultaneously CH, R is hydrogen, ($C_1$–$C_{12}$)-alkyl; ($C_2$–$C_{10}$)-alkenyl; ($C_2$–$C_{10}$)-alkynyl; ($C_1$–$C_6$)-alkyl, which is mono- to tetrasubstituted by radicals selected from the group consisting of halogen, ($C_1$–$C_4$)-alkoxy, ($C_1$–$C_4$)-alkylthio, CN, [($C_1$–$C_4$)-alkoxy]carbonyl and ($C_2$–$C_6$)-alkenyl; or ($C_3$–$C_8$)-cycloalkyl, which is unsubstituted or substituted by radicals selected from the group consisting of ($C_1$–$C_4$)-alkyl, ($C_1$–$C_4$)-alkoxy, ($C_1$–$C_4$)-alkylthio and halogen; ($C_5$–$C_8$)-cycloalkenyl; phenyl-($C_1$–$C_4$)-alkyl, which is unsubstituted in the phenyl radical or substituted in the phenyl radical by one or more radicals selected from the group consisting of halogen, ($C_1$–$C_4$)-alkyl, ($C_1$–$C_4$)-alkoxy, ($C_1$–$C_4$)-haloalkyl, ($C_1$–$C_4$)-alkylthio, [($C_1$–$C_4$)-alkoxy]carbonyl, [($C_1$–$C_4$)-alkyl] carbonyloxy, carboxamide, [($C_1$–$C_4$)-alkyl]-carbonylamino, [($C_1$–$C_4$)-alkyl]aminocarbonyl, di[($C_1$–$C_4$)-alkyl]-aminocarbonyl and nitro; or is a radical of the formulae A-1 to A-10

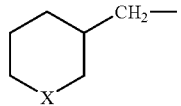
A-1

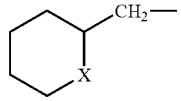
A-2

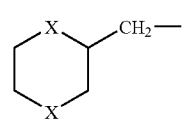
A-3

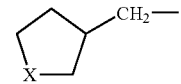
A-4

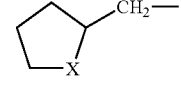
A-5

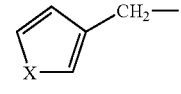
A-6

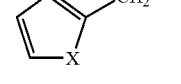
A-7

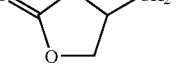
A-8

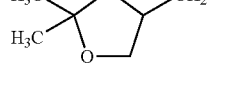
A-9

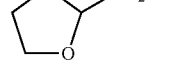
A-10 in which

X is O, S, S(O) or $SO_2$;

$R^1$ is hydrogen or ($C_1$–$C_3$)-alkyl;

$R^2$ is hydrogen, halogen, ($C_1$–$C_3$)-alkyl or ($C_1$–$C_3$)-alkoxy, where each of the two lastmentioned radicals is unsubstituted or mono- or polysubstituted by halogen or ($C_1$–$C_3$)-alkoxy;

$R^3$ is hydrogen, halogen, ($C_1$–$C_3$)-alkyl, ($C_1$–$C_3$)-alkoxy or ($C_1$–$C_3$)-alkylthio, where each of the three lastmentioned radicals is unsubstituted or mono- or polysubstituted by halogen or mono- or disubstituted by ($C_1$–$C_3$)-alkoxy or ($C_1$–$C_3$)-alkylthio; or is a radical of the formula $NR^5R^6$, ($C_3$–$C_6$)-cycloalkyl, ($C_2$–$C_4$)-alkenyl, ($C_2$–$C_4$)-alkynyl, ($C_3$–$C_4$)-alkenyloxy or ($C_3$–$C_4$)-alkynyloxy;

$R^4$ is hydrogen, ($C_1$–$C_4$)-alkyl or ($C_1$–$C_4$)-alkoxy and $R^5$ and $R^6$ independently of one another are hydrogen, ($C_1$–$C_4$)-alkyl, ($C_3$–$C_4$)-alkenyl, ($C_1$–$C_4$)-haloalkyl or ($C_1$–$C_4$)-alkoxy.

The salts of the compounds (I) are preferably compounds in which the hydrogen atom in the $SO_2NH$ group of the sulfonylurea has been replaced by a cation, preferably a physiologically acceptable cation which can be used in crop protection, in particular an alkali metal or alkaline earth metal cation or an optionally substituted ammonium ion, including quaternary ammonium ions. Examples of cations are the sodium, potassium and ammonium ions.

Salts of the compounds of the formula (I) can be formed by adding a suitable inorganic or organic acid, such as, for example, HCl, HBr, $H_2SO_4$ or $HNO_3$, or else oxalic acid or sulfonic acids, to a basic group, such as, for example, amino or alkylamino. Suitable substituents which are present in deprotonated form, such as, for example, sulfonic acids or carboxylic acids, can form inner salts with groups which for their part can be protonated, such as amino groups.

It is also possible to form salts by replacing the hydrogen of suitable functional groups, such as, for example, the carboxyl group, by an agriculturally suitable cation. These salts are, for example, metal salts, in particular alkali metal salts or alkaline earth metal salts, in particular sodium and potassium salts, or else ammonium salts, salts with organic amines or quaternary ammonium salts.

Of particular interest are compounds of the formula (I) or salts thereof in which the group of formula —CO—Q—R is ortho to the sulfonyl group of the sulfonylurea (I). Preference is given to compounds (I) or salts thereof in which Q=oxygen atom, X*=hydrogen or halogen, preferably iodine, R=$(C_1-C_4)$-alkyl; $(C_2-C_4)$-alkenyl; $(C_2-C_4)$-alkynyl; $(C_1-C_4)$-haloalkyl, or $(C_1-C_4)$-alkoxy$(C_1-C_4)$-alkyl, preferably methyl or ethyl, in particular methyl. Preference is furthermore given to compounds (I) and salts thereof in which the group of the formula —CO—Q—R is ortho to the sulfonyl group of the sulfonylurea, X*=halogen, preferably iodine, and X* is para to the group of the formula —CO—Q—R.

According to WO-A-92/13845, it is known to prepare the compounds (I) or salts thereof from appropriately substituted phenylsulfonyl isocyanates by reaction with heterocyclic amines, for example 2-amino-4-methoxy-6-methyl-1,3,5-triazine or 2-amino-4,6-dimethoxypyrimidine. The phenylsulfonyl isocyanates for their part can be obtained, for example, from the corresponding phenylsulfonyl chlorides by ammonolysis to sulfonamides and conversion of the sulfonamides into sulfonyl isocyanates by standard methods.

The ammonolysis can be carried out, for example, by dissolving the sulfonyl chloride in an organic solvent, such as tetrahydrofuran (THF), and introducing gaseous ammonia (cf. WO-A-92/13845).

A suitable standard method for preparing the substituted phenylsulfonyl isocyanate from the resulting phenylsulfonamide is the successive treatment of the phenylsulfonamide with thionyl chloride and phosgene, if appropriate in the presence of catalytic amounts of a base such as pryridine; cf. WO-A-92/13845, Example 11. Alternatively, the phenylsulfonamide can also be reacted with an alkyl isocyanate using sterically hindered amine bases as catalysts, to give the correspondingly substituted N-alkyl-N'-phenylsulfonylurea, which is then phosgenated to the substituted phenylsulfonyl isocyanate; cf. also WO-A-92/13845, Example 12. Comparable reactions have also been described for structurally different phenyl- or heteroarylsulfonamides for preparing the sulfonyl isocyanates; see, for example, U.S. Pat. No. 4,647303, EP-A-4602942, EP-A-0184385, EP-A-0727423.

Also known is the direct reaction of aryl- or heteroarylsulfonamides with phosgene in the presence of alkyl isocyanates or cycloalkyl isocyanates and, if appropriate, in the presence of sterically hindered amine bases (U.S. Pat. No. 4,647303, EP-A-0584043, EP-A-0030138, EP-A-0184385).

WO-A-96/06826 describes a process for the phosgenation of phenylsulfonamides, some of which also have orthocarbalkoxy groups on the phenyl ring, to give the correspondingly substituted phenylsulfonyl isocyanate by reaction with phosgene in the presence of a catalyst comprising butyl isocyanate and tertiary amines, such as DABCO, and/or comprising substituted sulfonyl isocyanates. In one example, the catalyst used is n-butyl isocyanate in combination with a small amount of the end product (as substituted sulfonyl isocyanate) from an earlier batch as cocatalyst. In the procedure preferred in this publication, there is a permanent excess of phosgene, based on the sulfonamide used.

The abovementioned known processes for preparing phenylsulfonamides, phenylsulfonyl isocyanates and compounds of formula (I) are, however, unsatisfactory with respect to chemical yields, space/time yields and/or the apparatus required. For example, in the case of phenylsulfonylureas having carbalkoxy groups in the 2-position on the phenyl radical, by-products, such as the corresponding saccharin derivative, are formed during ammonolysis.

In the phosgenation of the correspondingly substituted N-alkyl-N'-phenylsulfonylurea, significant amounts of substituted N,N'-bis(phenyl-sulfonyl)urea are frequently encountered as by-product. Moreover, relatively long reaction times are required for this phosgenation method, in particular for the initial phase (onset of the phosgenation). The preparation of the N-alkyl-N'-phenylsulfonylurea by the known method requires sterically hindered amine bases, the use and removal of which are associated with technical and economical expense.

Hitherto, only a few methods have been disclosed for the phenylsulfonyl isocyanates which are substituted in the phenyl radical by X*=halogen, preferably iodine, and which are preferably to be prepared (cf. WO-A-92/13845). Which method could improve the preparation of such compounds has hitherto not been known. Especially owing to the particular structural features of these compounds, such as, for example, sterical hindrance and reactivity at the substituted phenyl radical, only a few results can be expected analogously from processes with structurally different aryl- or heteroarylsulfonamides.

The reaction of the resulting sulfonyl isocyanates with heterocyclic amines to give compounds of the formula (I) can be carried out according to known methods by different routes.

In general, the reactions of phenylsulfonyl isocyanates with aminopyrimidines or aminotriazines can be carried out in an organic solvent. Solvents which are recommended for this purpose are polar aprotic solvents, such as THF and acetonitrile (see, for example, EP-A-0030138, pages 14–15).

SU 1233456 (1996) discloses the use of N-methylpyrrolidone (NMP) in an aprotic organic solvent for coupling aminotriazines with arylsulfonyl isocyanates. At a proportion of from 1 to 20% of NMP in the solvent xylene, yields of about 80 to 82% are achieved within a reaction time of 2 to 4 hours. The yields are unsatisfactory for application on an industrial scale.

According to U.S. Pat. No. 0,464,7303 and U.S. Pat. No. 0,460,2942, DABCO is used for accelerating the coupling reaction. The use of 1,4-diazabicyclo[2.2.2]octane (DABCO) on an industrial scale is disadvantageous since it has to be used in addition to the reactants and removed after the reaction at particular expense.

It is therefore an object of the present invention to provide an alternative process which, compared to the known processes, can be carried out advantageously with respect to one aspect, preferably a plurality of aspects.

The invention provides a process for preparing the abovementioned phenylsulfonylureas of the formula (I) and salts thereof, which comprises a) converting a compound of the formula (II)

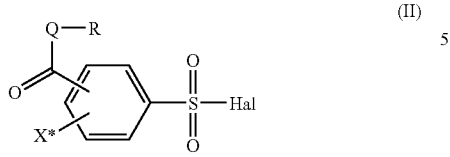
(II)

in which Hal is a halogen atom, preferably chlorine, bromine or iodine, in particular chlorine, and R, Q and X* are as defined in formula (I),
by ammonolysis with ammonia into the compound of the formula (III)

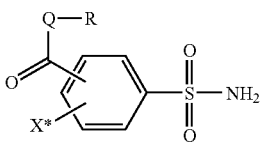
(III)

in which R, Q and X* are as defined in formula (I),
or preferably
(a1) carrying out the reaction in an organic solvent mixture comprising
(1) one or more optionally halogenated aromatic hydrocarbons, for example xylene, toluene, chlorobenzene or dichlorobenzene, and
(2) one or more polar aprotic solvents, preferably from the group consisting of nitriles, such as acetonitrile, and esters, preferably $(C_1-C_6)$-alkyl $(C_1-C_2)$-alkanecarboxylates, such as ethyl acetate, isopropyl acetate, n-butyl acetate, n-pentyl acetate and other amyl acetates, and ethers, such as tetrahydrofuran (THF) or 1,2-dimethoxyethane (DME), amides, such as dimethylformamide (DMF), ketones, such as acetone, methyl ethyl ketone or methyl isobutyl ketone (MIBK), and mixtures of two or more of the polar solvents,
in a weight ratio of solvent (1):solvent (2) of 20:1 to 1:1, preferably of 10:1 to 1.4:1, in particular carrying out the abovementioned preferred reaction with addition of a solution of the compound (II) in solvent (1) or a solvent mixture of solvents (1) and (2) to the concentrated or saturated solution of ammonia in solvent (2),
(b) reacting the resulting compound (III) with or without intermediate isolation with phosgene to give the phenylsulfonyl isocyanate of the formula (IV)

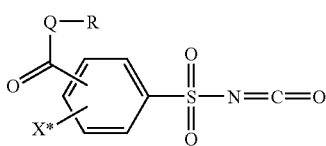
(IV)

in which R, Q and X* are as defined in formula (I),
or preferably
(b1) in the case X*=halogen, in particular X*=iodine, carrying out the reaction with phosgene in an organic solvent in the presence of an isocyanate of the formula $R^1$-NCO as catalyst, where $R^1$ is a hydrocarbon radical which is unsubstituted or substituted and including preferably from 1 to 20 carbon atoms, in particular from 1 to 16 carbon atoms, or a mixture of a plurality of these isocyanates as catalyst, preferably one or more isocyanates from the group consisting of N-alkyl isocyanates, N-cycloalkyl isocyanates and N-aryl isocyanates, preferably an N—$(C_1-C_{12})$-alkyl isocyanate from the group consisting of methyl isocyanate, ethyl isocyanate, n-propyl isocyanate, isopropyl isocyanate n-, iso-, sec- or tert-butyl isocyanate, pentyl isocyanate, hexyl isocyanate, heptyl isocyanate, cyclohexyl isocyanate and phenyl isocyanate, in particular n-butyl isocyanate or cyclohexyl isocyanate,
with or preferably without addition of an amine base or another base as cocatalyst, in particular initiating the reaction by initially charging an amount of the sulfonyl isocyanate of the formula (IV),
(c) reacting the resulting compound (IV) with or without intermediate isolation in an organic solvent with an amine of the formula (V)

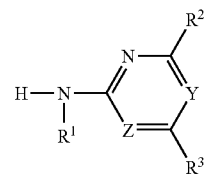
(V)

in which $R^1$, $R^2$, Y and Z are as defined in formula (I)
to give the sulfonylurea of the formula (I) or a salt thereof,
or preferably
(c1) carrying out the reaction in a solvent mixture of an optionally halogenated aromatic hydrocarbon having a boiling point of more than 110° C. and a polar aprotic solvent, preferably xylene/ethyl acetate or xylene/acetonitrile, where at least one of the preferred partial steps (a1), (b1) and (c1) is carried out in the process.

The invention also provides the novel partial steps (a1) and (c1) of the process and the partial step (b1) if X*=halogen, preferably iodine, and combined multi-step procedures or corresponding one-pot processes.

In the definitions of the formulae (I) to (V) and all subsequent formulae, the radicals alkyl, alkoxy, haloalkyl, haloalkoxy, alkylamino and alkylthio and the corresponding unsaturated and/or substituted radicals can in each case be straight-chain or branched in the carbon skeleton.

Unless specifically indicated, the lower carbon skeletons, for example having 1 to 6 carbon atoms, in particular 1 to 4 carbon atoms, or in the case of unsaturated groups having 2 to 6 carbon atoms, in particular 2 to 4 carbon atoms, are preferred in these radicals. Alkyl radicals, also in the combined meanings, such as alkoxy, haloalkyl and the like are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meanings of the possible unsaturated radicals which correspond to the alkyl radicals and which contain at least one double bond or triple bond, preferably one double bond or triple bond. Alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Cycloalkyl is a carbocyclic saturated ring system having preferably 3–8 carbon atoms, preferably 3 to 6 carbon atoms, for example cyclopropyl, cyclobutyl, cyclopentyl or cyclohexyl.

Halogen is, for example, fluorine, chlorine, bromine or iodine. In the radical definitions, "halogen" denotes a halogen radical, i.e. a halogen atom. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example monohaloalkyl (=monohalogeno alkyl), perhaloalkyl, $CF_3$, $CHF_2$, $CH_2F$, $CF_3CF_2$, $CH_2FCHCl$, $CCl3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

Aryl is a carbocyclic aromatic system, for example a mono-, bi- or polycyclic aromatic system, for example phenyl, naphthyl, tetrahydronaphthyl, indenyl, indanyl, pentalenyl, fluorenyl and the like, preferably phenyl.

A hydrocarbon radical contains exclusively carbon atoms and hydrogen atoms and can be straight-chain, branched or cyclic, saturated, unsaturated or aromatic, or can contain a combination of identical or different hydrocarbon radicals of those mentioned further above. "Hydrocarbon radical" includes, for example, the radicals alkyl, alkenyl, alkynyl, cycloalkyl, cycloalkenyl, cycloalkylalkyl, cycloalkenylalkyl, aryl, such as phenyl or naphthyl, benzyl, phenethyl, etc. A hydrocarbon radical preferably contains 1 to 30 carbon atoms, in particular 1 to 24 carbon atoms, unless defined otherwise.

If a skeleton is substituted "by one or more radicals" from a list of radicals (=group) or a generically defined group of radicals, this includes in each case the simultaneous substitution by a plurality of identical and/or structurally different radicals.

Substituted radicals such as a substituted hydrocarbon radical, for example a substituted alkyl, alkenyl, alkynyl, aryl, phenyl or benzyl radical, denote, for example, a substituted radical derived from the unsubstituted skeleton, the substituents being, for example, one or more, preferably 1, 2 or 3, radicals selected from the group consisting of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, alkylsulfinyl and alkylsulfonyl and, in the case of cyclic radicals, also alkyl, haloalkyl, alkylthioalkyl, alkoxyalkyl, optionally substituted mono- and dialkylaminoalkyl and hydroxyalkyl.

Preference is given to substituents from the group consisting of halogen, alkoxy, alkylthio, hydroxyl, amino, nitro, cyano, mono- and dialkylamino and, in the case of cyclic radicals, also alkyl and haloalkyl;

the term "substituted radicals", such as substituted hydrocarbon radicals, such as substituted alkyl etc., includes as substituents, in addition to the saturated hydrocarbon-containing radicals mentioned, corresponding unsaturated aliphatic and aromatic radicals, such as optionally substituted alkenyl, alkynyl, alkenyloxy, alkynyloxy, phenyl, phenoxy etc. Substituted cyclic radicals having aliphatic moieties in the ring also include cyclic systems having substituents which are attached to the ring via a double bond, for example those substituted by an alkylidene group, such as methylidene or ethylidene.

The substituents mentioned by way of example ("first substituent level") can, if they contain hydrocarbon-containing moieties, be, if appropriate, substituted further in these moieties ("second substituent level"), for example by one of the substituents defined for the first substituent level. Further corresponding substituent levels are possible. The term "substituted radical" preferably only embraces one or two substituent levels. For the substituents mentioned, preference is in each case given to the number of carbon atoms mentioned further above as being preferred for radicals having hydrocarbon moieties.

The compounds of the formula (II) are known or can be prepared by known methods. In this respect, particular reference made to the content of the publications EP-A-007687 and WO-A-92/13845 and the literature cited therein. With respect to the process procedures and the preferred compounds of the formula (I) and their precursors mentioned therein, the content of WO-A-92/13845 is intended to be incorporated into the present description and invention by way of reference.

Particularly preferred for the preparation process are compounds of the formula (II) in which Q=oxygen atom, X*=hydrogen or halogen, preferably iodine, R=($C_1$–$C_4$)-alkyl; ($C_2$–$C_4$)-alkenyl; ($C_2$–$C_4$)-alkynyl; ($C_1$–$C_4$)-haloalkyl, or ($C_1$–$C_4$)-alkoxy($C_1$–$C_4$)-alkyl, preferably methyl or ethyl, in particular methyl, and Hal=chlorine.

The ammonolysis of the sulfonyl chloride (II) can be carried out according to customary methods for ammonolyses, as described, for example, in handbooks for chemistry or in WO-A-92/13845. A customary method comprises the use of ammonia gas which is introduced into a solution of the sulfonyl chloride (II) in an organic solvent. Suitable organic solvents are, for example, polar aprotic solvents, such as THF or acetone. The reaction generally takes place even at room temperature. For work-up, the ammonium chloride that has been formed has to be separated from the product, which can be achieved by various methods known to the person skilled in the art.

In the ammonolysis process described in WO-A-92/13845, THF is used as the sole solvent. For relatively large amounts and on an industrial scale, the process cannot be carried out satisfactorily. Thus, in general, yields of less than 80% of theory are achieved, mainly due to the formation of by-products, for example saccharin (derivatives) by intramolecular reaction.

The invention provides an improved process for ammonolysis, specifically the process according to the preferred variant (a1) mentioned. According to the invention, the reaction is carried out in a solvent mixture of solvent (1) and solvent (2) in a weight ratio of solvent (1):solvent (2) of from 20:1 to 1:1, preferably from 10:1 to 1.4:1. This corresponds to a mixture of an optionally halogenated aromatic hydrocarbon to which from 5 to 100% by weight, preferably 10–71 percent by weight, of the polar solvent (2) have been added. Also according to the invention is the process where the reaction is initially started with a solvent (1) or (2) or a solvent mixture where the proportion of solvent (1) or (2) is not within the ratio by weight according to the invention, if addition of the apolar or polar solvent during the reaction results in a ratio according to the invention.

A particularly preferred solvent (1) is xylene. Preferred polar solvents (2) are acetonitrile, ethyl acetate, isopropyl acetate, acid, n-butyl acetate, tetrahydrofuran, 1,2- dimethoxyethane (DME), dimethylformamide, methyl ethyl ketone, methyl isobutyl ketone and mixtures of two or more of the polar solvents, in particular acetonitrile or ethyl acetate.

It is possible, for example, to initially charge the compound (II) in a mixture of solvents (1) and (2) and to introduce ammonia as a solution or as gas. Alternatively, the compound (II) can be initially charged in a solvent (1) and ammonia can be added as a solution in solvent (2). Furthermore, it is possible to initially charge ammonia in solution and to add a solution of the compound (II). Suitable are both a continuous addition of one of the reaction components or a batchwise addition. It is also possible to add both reaction components in parallel, continuously or a little at a time, to the reaction vessel.

The reaction is preferably carried out by adding a solution of the compound (II) in solvent (1) or in a solvent mixture of solvents (1) and (2) to the concentrated or saturated solution of ammonia in solvent (2). Particularly preferably, the ammonia that is consumed during the reaction is made up for by introducing ammonia gas, so that the reaction solution is always saturated with or contains a high concentration of ammonia.

The reaction temperature for the ammonolysis is, for example, in the range from −20° C. to the boiling point of the solvent or solvent mixture in question, preferably in the range from 0° C. to +80° C., in particular in the range from 20° C. to 60° C.

The reaction can be carried out at atmospheric pressure, but also at reduced or elevated pressure.

The compound (III) obtained after the ammonolysis (phenylsulfonamide) can be converted, with or without intermediate isolation, using phosgene to give the phenylsulfonyl isocyanate of the formula (IV). Conditions which are suitable for the reaction are customary conditions for preparing sulfonyl isocyanates from sulfonamides, for example the sequential treatment of the phenylsulfonamide with thionyl chloride and phosgene in the presence of catalytic amounts of a base, such as pyridine, mentioned at the outset and known from WO-A-92/13845.

Alternatively, according to a known procedure, the phenylsulfonamide can be reacted with an alkyl isocyanate in the presence of a sterically hindered organic base, such as 1,8-diazabicyclo[5.4.0]undec-7-ene (DBU), 1,4-diazabicyclo octane (DABCO) or 1,5-diazabicyclo[4.3.0]non-5-ene (DBN) as catalyst, to give a N-alkyl-N'-phenylsulfonylurea, which then reacts with phosgene to give the substitued phenylsulfonyl isocyanate; cf. WO-A-92/13845, Example 12. The analogous direct reaction in a one-pot process is described in EP-A-0030138.

However, in the preparation of the phenylsulfonyl isocyanates of the formula (IV), in which X*=halogen, preferably iodine, preferably of those compounds (IV) in which the group —CO—Q—R is ortho to the sulfonyl isocyanate group and in particular those in which the group X*=halogen is para to the group —CO—Q—R, the abovementioned known process alternatives generally do not give the desired yields and purities.

According to the invention, the disadvantages of the abovementioned known methods in the preparation of the preferred compounds (IV) can be avoided by reacting the appropriately substituted phenylsulfonamides of the formula (III) according to the preferred procedure (b1) with phosgene in an organic solvent in the presence of an isocyanate of the abovementioned formula R'-NCO as catalyst with or preferably without addition of an amine base or another base as cocatalyst to give the corresponding sulfonyl isocyanates of the formula (IV).

The process without addition of sterically hindered amine bases is preferred, because the amine bases otherwise have to be removed from the product at particular expense.

Organic solvents which are suitable for the phosgenation are, for example, aprotic organic solvents which are inert under the reaction conditions, preferably an optionally halogenated aromatic hydrocarbon, for example toluene, xylene, mesitylene, chlorobenzene, chlorotoluene or dichlorobenzene, a polar aprotic solvent from the group of the alkyl alkanecarboxylates, preferably from the group of the $(C_1–C_6)$-alkyl $(C_1–C_2)$-alkanecarboxylates, such as ethyl acetate, isopropyl acetate, n-butyl acetate, n-pentyl acetate and other amyl acetates, and mixtures of two or more of the solvents mentioned.

Preferably, the same solvents or solvent mixtures are used for steps (a) and (b) of the process.

The ratio of isocyanate of the formula R'-NCO to compound of the formula (III) can be varied within broad limits. From 5 to 100 mol %, preferably from 10 to 50 mol %, of isocyanate of the formula R'-NCO, based on the sulfonamide of the formula (III) used, are advantageous. In general, the reaction is initially delayed. Surprisingly, it has been found that the reaction rate can be increased considerably at the beginning if, as initial charge, a quantity of a sulfonyl isocyanate, preferably a catalytic amount of the sulfonyl isocyanate of the formula (IV) which is to be prepared, is employed. The advantageous quantity can be determined in preliminary experiments. In general, from 5 to 20 mol % of the compound (IV), based on the amount of sulfonamide (III), are sufficient as initial charge to substantially prevent a delayed onset of the reaction. For the phosgenation, it is possible, for example, to initially charge the compound (III) in an organic solvent together with the isocyanate of the formula R'-NCO, and to introduce phosgene. Alternatively, the isocyanate can be initially charged in an organic solvent, followed by introduction of phosgene and simultaneous, continuous or batchwise, addition of the sulfonamide of the formula (III). In the last-mentioned process, the concentration of the sulfonamide during the reaction is relatively low, thus reducing the amount of byproducts. Preference is given to the procedure where the isocyanate of the formula R'-NCO and some of the sulfonyl isocyanate (IV) are initially charged in an organic solvent, followed by introduction of phosgene.

The reaction temperature for the phosgenation is, for example, in the range from 50° C. to the boiling point of the solvent in question, preferably in the range from 100° C. to the boiling point of solvent in question, in particular from 100 to 180° C., very particularly from 120 to 140° C.

The reaction can be carried out under atmospheric pressure, elevated or reduced pressure. A phosgene partial pressure in the range from 0.2 to 20 bar, preferably from 1 to 6 bar, is advantageous.

To obtain the best possible conversion of the compound (III), phosgene is preferably employed in an amount of from 1 to 4 mol, in particular from 1 to 2.5 mol, per mole of the compound of the formula (III). During the reaction, an excess of phosgene is preferably present at all times. The phosgene content in the reaction mixture is preferably 2 percent by weight, in particular more than 5 percent by weight in the reaction mixture.

For work-up of the reaction mixture, the product (IV) can be isolated by customary methods, or else, preferably, the reaction mixture is employed directly, after removal of excess phosgene and isocyanate of the formula R'-NCO, for the conversion into the compound (I) (coupling reaction). The process according to the invention has the advantage that industrial work-up is simple, i.e. it is possible to remove simultaneously, by distillation of some of the solvent, if appropriate under reduced pressure, excess phosgene and the isocyanate of the formula R'-NCO.

Using the phosgenation (b1) according to the invention, yields of more than 90% of theory of compound (IV) are generally achieved, surprisingly also for phosgenations of compounds (III) having sterically demanding radicals (X*=chlorine, bromine, iodine), which tend to undergo side reactions. The compounds (IV) can be prepared by the preferred process without the use of an amine base as catalyst being required. The purities are sufficiently high for further processing. Removal of catalyst or corresponding salt and their work-up can be dispensed with. The solvents used can be separated off industrially in a simple manner and be re-used for further batches. Because of the features mentioned, the process is advantageous, both economically and ecologically.

The phosgenation according to the invention is also a preferred procedure for preparing compounds of the formula (IV) in which X* has a meaning other than halogen.

The compound (IV) obtained according to step (b) can be converted with or without intermediate isolation in an organic solvent with an amine of the formula (V) mentioned into the sulfonylurea of the formula (I) or its salts.

In general, the reactions of phenylsulfonyl isocyanates with aminopyrimidines or aminotriazines can be carried out in an organic solvent. Recommended solvents are, in general, polar aprotic solvents, such as THF and acetonitrile (see, for example, EP-A-0030138, pages 14–15). However, with respect to the reaction rates, yields and purities achieved, the reactions with compounds of the formula (IV) and amines of the formula (V) are frequently unsatisfactory. It is possible to increase the yield and reduce the reaction time by adding catalysts, such as sterically hindered amine bases; however, these have to be separated off after the reaction (see literature references mentioned at the outset).

According to the invention, it is possible to avoid the disadvantages mentioned by carrying out the reaction in a solvent mixture comprising an optionally halogenated aromatic hydrocarbon having a boiling point of more than 110° C., preferably 120–200° C., in particular 130 to 180° C., and a polar aprotic solvent, the ratio by weight of nonpolar solvent to polar solvent preferably being in the range from 20:1 to 1:10, in particular from 10:1 to 1:5, very particularly from 5:1 to 1:1.

Suitable relatively nonpolar solvents are toluene, xylene, chlorobenzene or dichlorobenzene or mixtures thereof, preferably o-, m- or p-xylene or the usual technical-grade xylene (industrial xylene mixture).

Preferred polar aprotic solvents are the polar solvents mentioned for process step (a), in particular the alkyl acetates or acetonitrile. Preference is given to mixtures of xylene/ethyl acetate or xylene/acetonitrile.

The reaction is preferably carried out at a temperature in the range from 0 to 100° C., preferably from 20 to 80° C., in particular from 40 to 70° C.

Preferably from 1 to 1.2 mol, in particular from 1 to 1.1 mol, very particularly from 1 to 1.05 mol of amine of the formula (V) are employed per mole of sulfonyl isocyanate of the formula (IV).

Using the process according to variant (c1), which is preferred according to the invention, it is possible to use equivalent amounts or virtually equivalent amounts of the compounds (IV) and (V). If other solvents are chosen, for example if a solvent is used instead of the solvent mixture to be used according to the invention, the conversion is generally incomplete, or a relatively large excess of compound (V) has to be employed to achieve conversion of the compound (IV). Moreover, in cases where only one solvent is used, the reaction rate is frequently unsatisfactorily low. In contrast, the procedure according to the invention in most cases affords a product with excellent yield and purity.

Work-up of the reaction mixture from the coupling can be carried out by customary methods, the sulfonylureas of the formula (I) being isolated either as non-salts or—after reaction with bases—as salts.

Particular preference is given to the process in which the preferred process steps (a1), (b1) and (c1) are carried out in combination. If the same solvent mixtures are used, one-pot reactions are possible.

In the examples below, the amounts stated are based on weight, unless other definitions are specifically indicated.

Example 1a

Methyl 2-amidosulfonyl-4-iodobenzoate

At 18–22° C., a total of 9.1 g of gaseous ammonia is introduced into a solution of 73 g of methyl 2-chlorosulfonyl-4-iodobenzoate (98.7%) in 189 g of xylene and 150 g of acetonitrile over a period of 1 hour. With stirring, nitrogen is then passed through the suspension for 1 hour. Remaining ammonia is removed by distilling off a little solvent under reduced pressure. The mixture is heated to reflux and filtered whilst still hot, and the residue is decomp. to exhaustion with fresh acetonitrile. The combined filtrates are concentrated distillatively and the cold residue is filtered. This gives 66.8 g of white needles of methyl 2-amidosulfonyl-4-iodobenzoate.

Example 1b (Comparative example)

If the reaction according to Example 1a is carried out in pure xylene instead of the xylene/acetonitrile mixture, after a reaction time of 6 hours and otherwise identical conditions a yield of 56.6 g of methyl 2-amidosulfonyl-4-iodobenzoate of a purity of only 83.3% (yield 69.1% of theory) is obtained.

Example 2a

Methyl 2-amidosulfonyl-4-iodobenzoate

With stirring, a solution of 144.2 g of methyl 2-chlorosulfonyl-4-iodobenzoate in 217.4 g of xylene and 150 g of ethyl acetate is metered at 35 to 37° C. and over a period of 4 hours into a saturated solution of ammonia in ethyl acetate (156.5 g). Simultaneously, a total of 16.7 g of ammonia are introduced at the rate of its consumption. The mixture is stirred for 1 extra hour, excess ammonia is removed by incipient distillation under reduced pressure and the mixture is heated to reflux and filtered while still hot. The filtercake is decomp. to exhaustion with boiling ethyl acetate. Most of the ethyl acetate is then distilled off, and the remaining suspension of the product in xylene is cooled to 20° C. Filtration and drying under reduced pressure gives 132.2 g of methyl 2-amidosulfonyl-4-iodobenzoate (purity 99.3%).

Example 2b (Comparative Example)

If the reaction according to Example 2a is carried out in a mixture of xylene/methanol (4:1), under otherwise identical conditions, a yield of 118.8 g of methyl 2-amidosulfonyl-4-iodobenzoate of a purity of 71% (yield 62% of theory) is obtained after work-up.

Example 3

Methyl 2-amidosulfonyl-4-iodobenzoate

Example 2a is repeated, but using a solution of the sulfonyl chloride in 300 g of xylene and 75 g of ethyl acetate instead of a solution of the sulfonyl chloride in 217.4 g of xylene and 150 g of ethyl acetate. This gives 130 g of methyl 2-amidosulfonyl-4-iodobenzoate (purity 99%).

Example 4

Methyl 2-amidosulfonyl-4-iodobenzoate

Example 2a is repeated, but using a solution of the sulfonyl chloride in 300 g of xylene and 75 g of acetonitirile instead of a solution of the sulfonyl chloride in 217.4 g of xylene and 150 g of ethyl acetate. This gives 131 g of methyl 2-amidosulfonyl-4-iodobenzoate (purity 99%).

Example 5a

Methyl 4-iodo-2-isocyanatosulfonylbenzoate

Under nitrogen protective gas, 150 ml of dry xylene and 6.84 ml of n-butyl isocyanate are heated to 126–128° C. Phosgene (a total of 50 g) is then initially introduced via the surface. The phosgene stream is regulated such that the temperature of the reaction mixture stays at 126–128° C. If required, introduction of phosgene is reduced or interrupted. Phosgene which escapes from the reaction mixture is condensed using a condenser cooled to −20° C. and passed back into the reaction mixture.

During the introduction of phosgene, 90 g of methyl 2-amidosulfonyl-4-iodobenzoate, as a suspension in 336 ml of xylene, are added a little at a time with stirring, over a period of 20 hours. After a further 10 hours of stirring under a phosgene-saturated atmosphere, 300 ml of a mixture of n-butyl isocyanate and xylene are distilled off at the same reaction temperature and under reduced pressure (100 to 120 mbar, 78 to 80° C.), and 400 ml of dry xylene are added in three portions during the distillation. The yield of the title compound is 92.8% of theory.

Example 5b (Comparative example)

The process according to Example 5a is repeated without addition of an alkyl isocyanate (for example butyl isocyanate); however, the added methyl 2-amidosulfonyl-4-iodobenzoate is not converted.

Example 6a

Methyl 4-iodo-2-isocyantosulfonylbenzoate (using an initial charge)

Under nitrogen protective gas, 3.73 ml of n-butyl isocyanate and 250 ml of xylene are added to a solution of methyl 4-iodo-2-isocyanatosulfonylbenzoate (19.7 g as a 14.8% strength solution in xylene). With stirring, the mixture is heated to 126–128° C., and phosgene is added via the surface. The phosgene stream is regulated such that the temperature of the reaction mixture stays at 126–128° C. If required, the addition of phosgene is reduced or interrupted. Phosgene which escapes from the reaction mixture is condensed using a condenser cooled to −20° C. and passed back into the reaction mixture. At the same time 90 g of methyl 2-amidosulfonyl-4-iodobenzoate, as a suspension in 216 ml of xylene, are added with stirring, a little at a time over a period of 10 hours. After a further 10 hours of stirring in a phosgene-saturated atmosphere at the same reaction temperature, 300 ml of a mixture of n-butyl isocyanate and xylene are distilled off under reduced pressure, and 433 ml of dry xylene are added during the distillation. The yield of the title compound is 94.8% of theory.

Example 6b (Comparative example)

The process according to Example 6a is repeated correspondingly, but without an additional charge of a solution of methyl 4-iodo-2 isocyanatosulfonyl-benzoate. After a reaction time of 20 hours, the reaction is still incomplete, the yield of methyl 4-iodo-2-isocyanatosulfonyl-benzoate being 86% of theory.

Example 7a (Coupling)

Methyl 4-iodo-2-{N-[N-(4-methoxy-6-methyl-1,3,5-triazin-2-yl)-aminocarbonyl]aminosulfonyl}benzoate Under protective gas, a 14.5% strength solution (1465 g) of methyl 4-iodo-2-isocyanatosulfonylbenzoate in xylene is added over 4 hours at a constant rate at 50° C. to a suspension of 84.5 g of 2-amino-4-methoxy-6-methyl-1,3,5-triazine in 670 g of ethyl acetate. After the addition has ended, the mixture is stirred at the same temperature for approximately 4 hours, and the ethyl acetate is then distilled off under reduced pressure (80–60 mbar, T=50° C.). The suspension that remains is filtered off with suction and the solid is washed repeatedly with dilute hydrochloric acid and dried; if appropriate, acetone can be added to the hydrochloric acid. This gives 297 g (content>98%) of the title compound; yield 99.2% of theory.

Example 7b (Comparative example)

The process according to Example 7a is repeated correspondingly using pure toluene as solvent. After 24 hours, the reaction is still incomplete. The title compound is obtained in a yield of 81% of theory and a purity of 89%.

What is claimed is:

1. A process for preparing the compound of the formula (I) or salt thereof

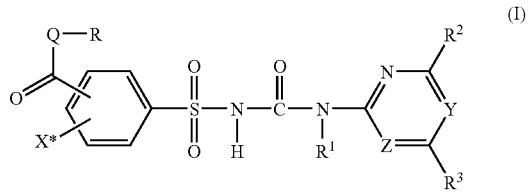

in which

Q is oxygen, sulfur or —N(R⁴)—,

X* is hydrogen, halogen, cyano, nitro, $(C_1–C_3)$-alkyl or methoxy,

Y, Z independently of one another are CH or N, where Y and Z are not simultaneously CH, R is hydrogen, $(C_1–C_{12})$-alkyl; $(C_2–C_{10})$-alkenyl; $(C_2–C_{10})$-alkynyl; $(C_1–C_6)$-alkyl, which is mono- to tetrasubstituted by radicals selected from the group consisting of halogen, $(C_1–C_4)$-alkoxy, $(C_1–C_4)$-alkylthio, CN, [$(C_1–C_4)$-alkoxy]carbonyl and $(C_2–C_6)$-alkenyl; or $(C_3–C_8)$-cycloalkyl, which is unsubstituted or substituted by radicals selected from the group consisting of $(C_1–C_4)$-alkyl, $(C_1–C_4)$-(alkoxy), $(C_1–C_4)$-alkylthio and halogen; $(C_5–C_8)$-cycloalkenyl; phenyl-$(C_1–C_4)$-alkyl, which is unsubstituted in the phenyl radical or substituted in the phenyl radical by one or more radicals selected from the group consisting of halogen, $(C_1–C_4)$-alkyl, $(C_1–C_4)$-alkoxy, $(C_1–C_4)$-haloalkyl, $(C_1–C_4)$-alkylthio, [$(C_1–C_4)$-alkoxy]carbonyl, [$(C_1–C_4)$-alkyl]carbonyloxy, carboxamide, [$(C_1–C_4)$-alkyl]-carbonylamino, [$(C_1–C_4)$-alkyl]aminocarbonyl, di[$(C_1–C_4)$-alkyl]-aminocarbonyl and nitro; or is a radical of the formulae A-1 to A-10

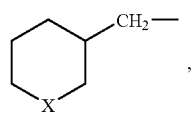
A-1

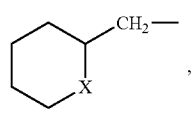
A-2

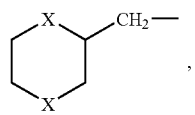
A-3

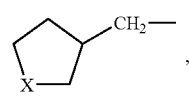
A-4

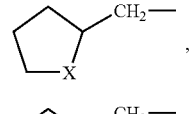
A-5

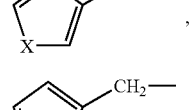
A-6

A-7

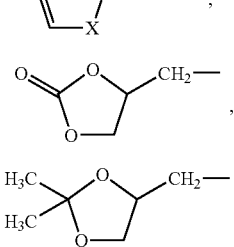
A-8,

A-9

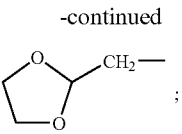
A-10 in which x is O, S, S(O) or $SO_2$;

$R^1$ is hydrogen or $(C_1–C_3)$-alkyl;

$R^2$ is hydrogen, halogen, $(C_1–C_3)$-alkyl or $(C_1–C_3)$-alkoxy, where each of the two lastmentioned radicals is unsubstituted or mono- or polysubstituted by halogen or $(C_1–C_3)$-alkoxy;

$R^3$ is hydrogen, halogen, $(C_1–C_3)$-alkyl, $(C_1–C_3)$-alkoxy or $(C_1–C_3)$-alkylthio, where each of the three lastmentioned radicals is unsubstituted or mon- or polysubstituted by halogen or mono- or disubstituted by $(C_1–C_3)$-alkoxy or $(C_1–C_3)$-alkylthio; or is a radical of the formula $NR^5R^6$, $(C_3–C_6)$-cycloalkyl, $(C_2–C_4)$-alkenyl, $(C_2–C_4)$-alkynyl, $(C_3–C_4)$-alkenyloxy or $(C_3–C_4)$-alkynyloxy;

$R^4$ is hydrogen, $(C_1–C_4)$-alkyl or $(C_1–C_4)$-alkoxy and $R^5$ and $R^6$ independently of one another are hydrogen, $(C_1–C_4)$-alkyl, $(C_3–C_4)$-alkenyl, $(C_1–C_4)$haloalkyl or $(C_1–C_4)$-alkoxy, which comprises a) converting a compound of the formula (II)

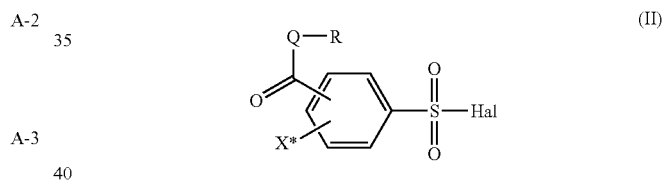
(II)

in which Hal is a halogen atom and R, Q and X* are as defined in formula (I), by ammonolysis with ammonia into the compound of the formula (III)

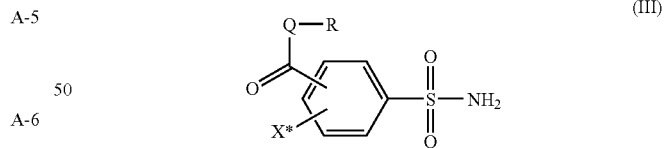
(III)

in which R, Q and X* are as defined in formula (I), or (a1) ammonolyzing the compound of the formula (II) to give the compound of formula (III) and carrying our the reaction in an organic solvent mixture comprising (1) one or more optionally halogenated aromatic hydrocarbons [solvent(1)] and (2) one or more polar aprotic solvents [(solvent (2)] in a weight ratio of solvent (1):solvent (2) of 20:1 to 1:1;

(b) reacting the resulting compound (III) with or without intermediate isolation with phosgene to give the phenylsulfonyl isocyanate of the formula (IV)

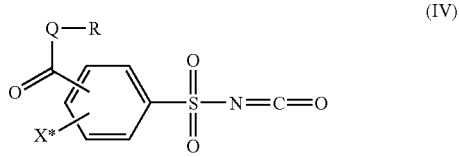

in which R, Q and X* are as defined in formula (I), or (b1) in the case X*=halogen, reacting the resulting compound (III) with or without intermediate isolation with phosgene to give the phenylsulfonyl isocyanate of the formula (IV) and carrying out the reaction with phosgene in an organic solvent in the presence of an isocyanate of the formula $R^1$-NCO as catalyst, where $R^1$ is a hydrocarbon radical which is unsubstituted or substituted, or a mixture of a plurality of these isocyanates as catalyst without addition of an amine base; and (c) reacting the resulting compound (IV) with or without intermediate isolation in an organic solvent with an amine of the formula (V)

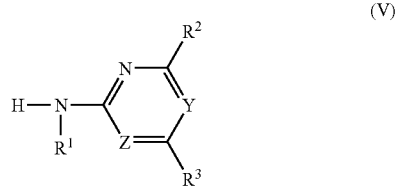

in which $R^1$, $R^2$, Y and Z are as defined in formula (I) to give the sulfonylurea of the formula (I) or a salt thereof, or (c1) reacting the resulting compound (IV) with or without intermediate isolation in an organic solvent with an amine of the formula (V) to give the compound of the formula (I) or a salt thereof, and carrying out the reaction in a solvent mixture of an optionally halogenated aromatic hydrocarbon having a boiling point of more than 110° and a polar aprotic solvent;

where at least one of the steps (a1) to (c1) is carried out in the process.

2. The process as claimed in claim 1, wherein in the formula (I) or a salt thereof Q is an oxygen atom, X* is hydrogen atom or halogen atom, R is $(C_1-C_4)$-alkyl; $(C_2-C_4)$-alkenyl; $(C_2-C_4)$-alkynyl; $(C_1-C_4)$-haloalkyl or $(C_1-C_4)$-alkoxy$(C_1-C_4)$-alkyl, $R^1$ is a hydrogen atom, $R^2$ is $(C_1-C_4)$-alkyl or $(C_1-C_4)$-alkoxy, $R^3$ is $(C_1-C_4)$-alkyl or $(C_1-C_4)$-alkoxy, Y is a nitrogen atom and Z is a nitrogen atom or a group of the formula CH.

3. The process as claimed in claim 2, wherein in the formula (I) or a salt thereof X* is an iodine atom, R is methyl or ethyl, $R^2$ is methoxy, $R^3$ is methyl and Z is a nitrogen atom.

4. The process as claimed claim 1, wherein the reaction in step (a1) is carried out in an organic solvent mixture comprising (1) one or more optionally halogenated aromatic hydrocarbons selected from the group consisting of xylene, toluene, chlorobenzene and dichlorobenzene [solvent (1)] and (2) one or more polar aprotic solvents [solvent (2)] selected from the group consisting of nitriles, esters, ethers, amides, ketones and mixtures of two or more of the polar solvents.

5. The process as claimed in claim 1, wherein the reaction in step (B1) is carried out in the presence of one or more isocyanates selected from the group consisting of N-alkyl isocyanates, N-cycloalkyl isocyanates and N-aryl isocyanates as catalyst.

6. The process as claimed in claim 5, wherein the reaction in step (b1) is carried out in the presence of n-butyl isocyanate or cyclohexyl isocyanate as catalyst.

7. The process as claimed in claim 1, wherein the reaction in step (c1) is carried out in xylene/ethyl acetate or xylene/acetonitrile.

8. A process for preparing a compound of formula (III)

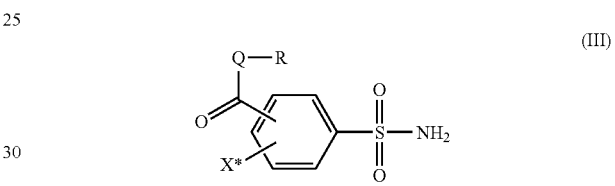

in which R, Q and X* are as defined in formula (I) according to claim 1, which comprises converting a compound of the formula (II)

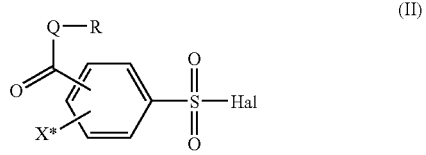

in which Hal is a halogen atom and R, Q and X* are as defined in formula (II) by ammonolysis with ammonia into the compound of the formula (III) and carrying out the reaction in an organic solvent mixture comprising (1) one or more optionally halogenated aromatic hydrocarbons [solvent(1)] and (2) one or more polar aprotic solvents [(solvent (2)] in a weight ratio of solvent (1):solvent (2) of 20:1 to 1:1.

9. A process for preparing a compound of the formula (IV)

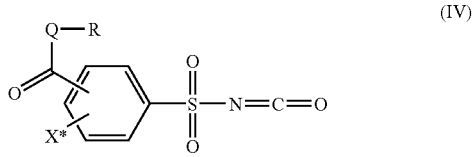

in which R and Q are as defined in formula (I) according to claim 11 and X* is halogen, which comprises reacting a compound of the formula (III)

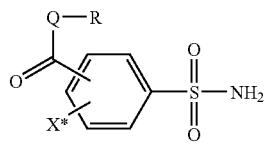
(III)

in which R, Q and X* are as defined in formula (II)

with phosgene in an organic solvent in the presence of one or more isocyanates of the formula R¹-NCO as catalyst, where R¹ is a hydrocarbon radical which is unsubstituted or substituted, without addition of an amine base or another base as cocatalyst, to give the phenylsulfonyl isocyanate of the formula (IV).

10. A process for preparing a compound of the formula (I) or salt thereof as defined in claim 1, which comprises reacting a compound of the formula (IV)

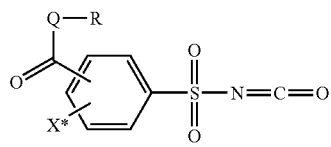
(IV)

in which R, Q and X* are as defined in formula (I)

with an amine of the formula (V)

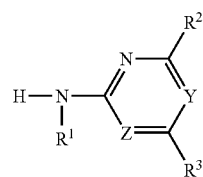
(V)

in which R¹, R², Y and Z are as defined in formula (I)

in a solvent mixture of an optionally halogenated aromatic hydrocarbon having a boiling point of more than 110° C. and a polar aprotic solvent to give a sulfonylurea of the formula (I) or a salt thereof.

11. A process for preparing a compound of the formula (I) or salt thereof as defined in claim 1, which comprises (b) reacting a compound of the formula (III)

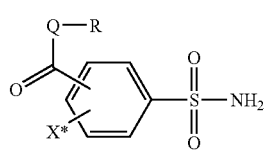
(III)

in which R, Q and X* are as defined in formula (I)

with phosgene to give the phenylsulfonyl isocyanate of the formula (IV)

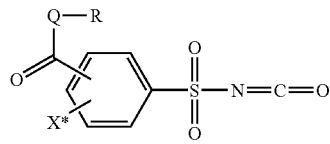
(IV)

in which R, Q and X* are as defined in formula (I), or (b1) in the case X*=halogen, reacting the compound of the formula (II) with phosgene to give the phenylsulfonyl isocyanate of the formula (IV) and carrying out the reaction with phosgene in an organic solvent in the presence of an isocyanate of the formula R¹-NCO as catalyst, where R¹ is a hydrocarbon radical which is unsubstituted or substituted, or a mixture of a plurality of these isocyanates as catalyst without addition of an, amine base; and (c) reacting the resulting compound (IV) with or without intermediate isolation in an organic solvent with an amine of the formula (V)

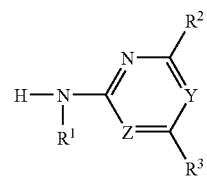
(V)

in which R¹, R², Y and Z are as defined in formula (I) to give the sulfonylurea of the formula (I) or a salt thereof, or (c1) reacting the resulting compound (IV) with or without intermediate isolation in an organic solvent with an amine of the formula (V) to give the compound of the formula (I) or a salt thereof and carrying out the reaction in a solvent mixture of an optionally halogenated aromatic hydrocarbon having a boiling point of more than 110° C. and a polar aprotic solvent, where at least one of the steps (b1) and (c1) is carried out in the process.

12. The process as claimed in any of claims 1 to 11, wherein on the phenyl ring the group —CO—Q—R is ortho to the substituted sulfonyl group, the group X*=halogen is para to the group —CO—Q—R.

13. The process of claim 12, wherein X is iodine.

14. The process of claim 1, wherein in step (a1) the weight ratio of solvent (1):solvent (2) is in the range of 10:1 to 1.4:1.

15. The process as claimed in claim 2, wherein the reaction in step (a1) is carried out in an organic solvent mixture comprising (1) one or more optionally halogenated aromatic hydrocarbons selected from the group consisting of xylene, toluene, chlorobenzene and dichlorobenzene [solvent (1)] and (2) one or more polar aprotic solvents [solvent (2)] selected from the group consisting of nitrites, esters, ethers, amides, ketones and mixtures of two or more of the polar solvents.

16. The process as claimed in claim 15, wherein the reaction in step (B1) is carried out in the presence of one or more isocyanates selected from the group consisting of N-alkyl isocyanates, N-cycloalkyl isocyanates and N-aryl isocyanates as catalyst.

17. The process as claimed in claim 16, wherein the reaction in step (b1) is carried out in the presence of n-butyl isocyanate or cyclohexyl isocyanate as catalyst.

18. The process as claimed in claim 16, wherein the reaction in step (c1) is carried out in xylene/ethyl acetate or xylene/acetonitrile.

19. The process as claimed in claim 18, wherein in the formula (I) or a salt thereof X* is an iodine atom,
R is methyl or ethyl,
$R^2$ is methoxy,
$R^3$ is methyl and
Z is a nitrogen atom.

20. The process as claimed in claim 19, wherein in step (a1) the weight ratio of solvent (1):solvent (2) is in the range of 10:1 to 1.4:1.

* * * * *